(12) United States Patent
Nishi et al.

(10) Patent No.: US 7,025,945 B2
(45) Date of Patent: Apr. 11, 2006

(54) TRANSITION METAL ACETYLIDE COMPOUND, NANO-POWDER AND METHOD FOR PRODUCING A TRANSITION METAL ACETYLIDE COMPOUND

(75) Inventors: Nobuyuki Nishi, Okazaki (JP); Kentaro Kosugi, Okazaki (JP)

(73) Assignee: Inter-University Research Institute Corporation National Institutes of Natural Sciences, Okazaki (JP)

( * ) Notice: Subject to any disclaimer, the term of this patent is extended or adjusted under 35 U.S.C. 154(b) by 0 days.

(21) Appl. No.: 10/944,037

(22) Filed: Sep. 20, 2004

(65) Prior Publication Data

US 2005/0171370 A1    Aug. 4, 2005

(30) Foreign Application Priority Data

Feb. 3, 2004    (JP) .............................. 2004-026797

(51) Int. Cl.
*C01B 31/00* (2006.01)
*C07F 15/00* (2006.01)
(52) U.S. Cl. .................. 423/414; 556/140; 977/DIG. 1
(58) Field of Classification Search ................ 423/414; 556/140
See application file for complete search history.

(56) References Cited

U.S. PATENT DOCUMENTS

2004/0028948 A1*    2/2004    Nishi ..................... 428/694 R

OTHER PUBLICATIONS

Nishi et al., Chemical Physics Letters, vol. 369, No. 1-2, pp. 198-203 (2003), Available on the Web Jan. 15, 2003.*

* cited by examiner

*Primary Examiner*—Porfirio Nazario-Gonzalez
(74) *Attorney, Agent, or Firm*—Oliff & Berridge, PLC

(57) ABSTRACT

An anhydrous chloride with a formula of $MCl_2$ (M=Fe, Co or Ni) is dissolved into an anhydrous acetonitrile solvent to form a chloride-acetonitrile solution. Then, calcium carbide minute powders are added and dispersed in the chloride-acetonitrile solution at a molar quantity equal to or smaller by 1–30 mol % than the molar quantity of the anhydrous chloride to form a reactive solution. Then, the reactive solution is heated at a predetermined temperature to chemically react the anhydrous chloride with the calcium carbide minute powders in the reactive solution to form a transition metal acetylide compound having an $M$-$C_2$-$M$ bond, a tetragonal structure, and a formula of $MC_2$ (herein, M=Fe, Co or Ni).

17 Claims, 3 Drawing Sheets

TRANSITION METAL ACETYLIDE COMPOUND, NANO-POWDER AND METHOD FOR PRODUCING A TRANSITION METAL ACETYLIDE COMPOUND

BACKGROUND OF THE INVENTION

1. Field of the Invention

This invention relates to a transition metal acetylide compound, a nano-powder and a method for producing a transition metal acetylide compound.

2. Description of the Related Art

Recently, an attention is paid to oxide nano-powders made of $\gamma\text{-Fe}_2\text{O}_3$ with ferromagnetic property to be employed as magnetic recording media. Ordering the sizes of the oxide nano-powders uniformly, however, is difficult, and the compositions of the oxide nano-powders may be changed so that in the oxide nano-powders, the ferromagnetic property relating to the composition of the $\gamma\text{-Fe}_2\text{O}_3$ is changed with time to the paramagnetic property relating to the composition of the $\alpha\text{-Fe}_2\text{O}_3$. As a result, it is difficult to practically use the oxide nano-powders for high density recording media.

In this point of view, carbon layer-covering transition metallic nano-structures are proposed, wherein the transition metallic nano-powders are covered with the respective carbon layers. In the carbon layer-covering transition metallic nano-structures, since the transition metallic nano-powders with ferromagnetic property are covered with the carbon layers, the transition metallic nano-powders can hold the ferromagnetic property for a long time.

However, the producing method for the carbon layer-covering transition metallic nano-powders has not established yet, and there are some problems in controlling the sizes of the nano-powders and the like.

SUMMERY OF THE INVENTION

It is an object of the present invention to provide a new nano-powder to be functioned as a precursor for a carbon layer-covering transition metallic nano-structure and a new compound constituting the nano-powder.

For achieving the above object, this invention relates to a nano-powder including a transition metal acetylide compound having an $\text{M-C}_2\text{-M}$ bond, a tetragonal structure, and a formula of $\text{MC}_2$ (herein, M=Fe, Co or Ni).

This invention also relates to a transition metal acetylide compound comprising:

an $\text{M-C}_2\text{-M}$ bond, a tetragonal structure, and a formula of $\text{MC}_2$ (herein, M=Fe, Co or Ni).

The transition metal acetylide compound according to the present invention includes a tetragonal structure such as $\text{CaC}_2$ or $\text{MgC}_2$, and thus, includes a transition metallic positive ion ($\text{M}^{2+}$) and a carbon molecule negative ion ($\text{C}_2^{2-}$). The carbon molecule negative ion has a strong reducing power, and for example, reduces the transition metallic positive ion into the neutral transition metal over 200° C. while the carbon molecule negative ion is oxidized into the neutral carbon radical ($\text{C}_2$ radical). The transition metal is bonded with the adjacent same transition metals, and the carbon radical is bonded with the adjacent same carbon radicals.

As a result, when the nano-powders made of the transition metal acetylide compound according to the present invention are heated over 200° C., the metallic cores are formed from the bonded transition metals, and the carbon shells (carbon layers) are formed from the bonded carbon radicals. As a result, an intended carbon layer-covering transition metallic nano-structures can be provided.

The size of each nano-powder can be controlled easily commensurate with the producing method of the nano-powder which will be described in detail hereinafter. On the other hand, since each carbon layer-covering transition metallic nano-structure can be formed by heating each nano-powder, e.g., with convergent electron beams, the size of each carbon layer-covering transition metallic nano-structure can be easily controlled commensurate with the easy controllability of each nano-powder as mentioned above.

The particle size of each nano-powder can be reduced to 5 nm or below.

The transition metal acetylide compound exhibits ferromagnetic property. Then, in the nano-powder made of the transition metal acetylide compound of the present invention, if the nano-powder is made of iron acetylide or cobalt acetylide, the nano-powder can exhibits super paramagnetic property when the size of the single crystal domain of the nano-powder is set to 5 nm or below. Also, the nano-powder can exhibit ferromagnetic property at room temperature when the size of the single crystal domain of the nano-powder is set within 5–300 nm, so that the nano-powders can be utilized for a room temperature magnet. If the nano-powder is made of nickel acetylide, the nano-powder can exhibit ferromagnetic property below a temperature of 10K.

Therefore, the carbon layer-covering transition metal nano-structure can exhibit ferromagnetic property or super paramagnetic property commensurate with the magnetic property of the nano-powder because the nano-structure is made of the nano-powder. Particularly, the nano-structure can be utilized as a single domain magnet when the nano-structure is made of the nano-powder made of the iron acetylide or the cobalt acetylide. As a result, the carbon layer-covering transition metallic nano-structure can be preferably used as a magnetic recording medium material.

The carbon layer-covering transition metallic nano-structure made of the transition metal acetylide compound is formed as a minute particle, so that the nano-structure can be employed for an electron transfer wire, a magnetic toner for copying machine and a contrast fortifier in magnetic resonance image photograph, in addition to for a magnetic recording medium material (recording element unit). The nano-structure can be also employed for a hydrogen absorbing nano-powder when a rare metal is contained in the nano-structure.

As mentioned above, according to the present invention can be provided a new nano-powder to be functioned as a precursor for a carbon layer-covering transition metallic nano-structure and a new compound constituting the nano-powder.

BRIEF DESCRIPTION OF THE DRAWINGS

For better understanding of the present invention, reference is made to the attached drawings, wherein.

DESCRIPTION OF THE PREFERRED EMBODIMENTS

Other features and advantages of the present invention will be described hereinafter.

Figure 1:
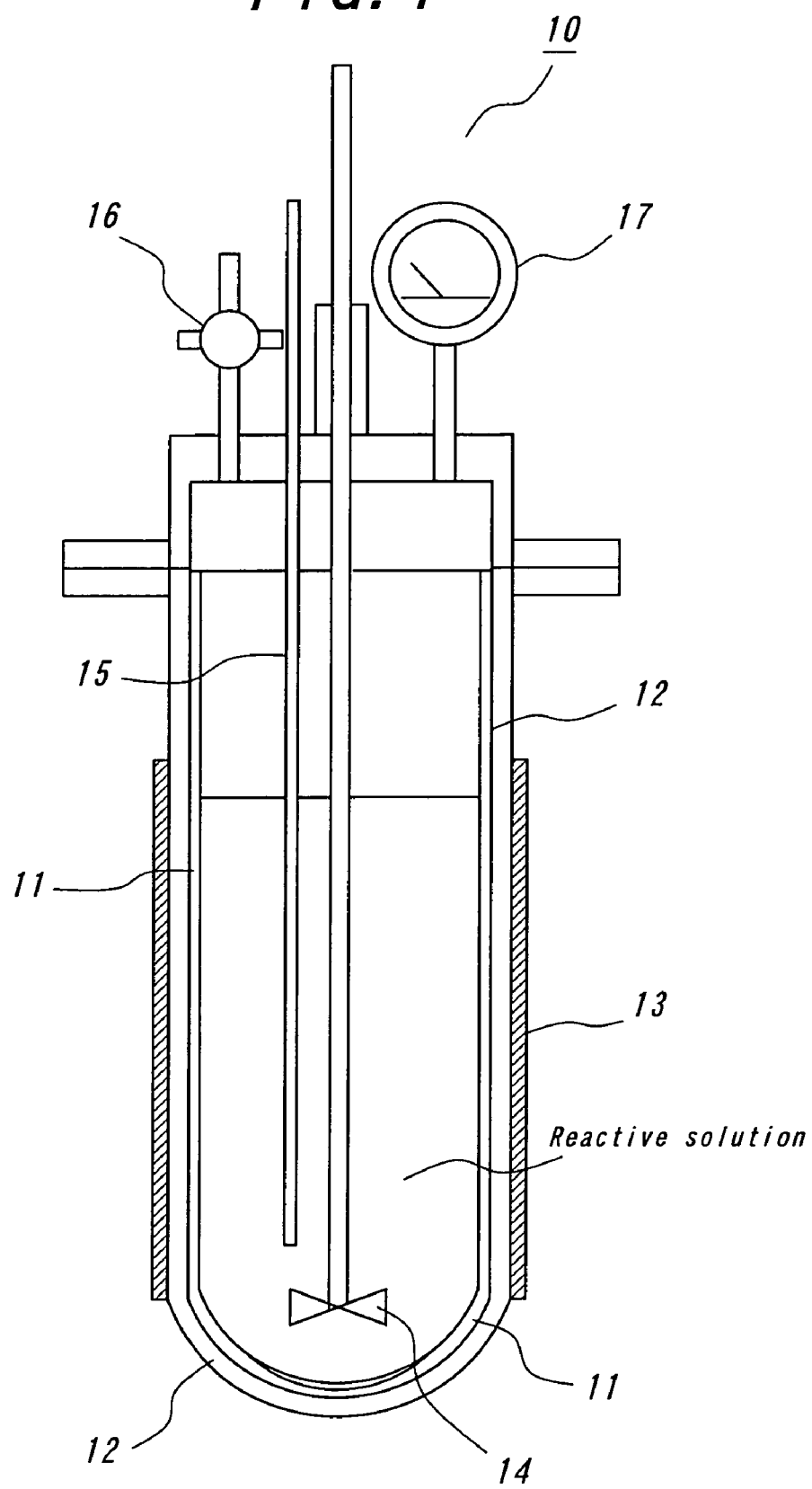
FIG. 1 is a structural view illustrating an apparatus to be employed in producing nano-powders made of a transition metal acetylide compound according to the present invention.

FIG. 1 is a structural view illustrating an apparatus to be employed in producing nano-powders made of a transition metal acetylide compound according to the present invention. The apparatus 10 illustrated in FIG. 1 includes a glass vessel 11 to charge a given reactive solution and a pressure tight case 12 made of stainless steel which is disposed outside from the glass vessel 11. A heater 13 is disposed on the periphery of the pressure tight case 12, and a rotator 14 and a temperature sensor 15 are disposed on the bottom of the glass vessel 11. A gas inlet 16 and a pressure gauge 17 are provided at the pressure tight case 12.

In the present invention, first of all, an anhydrous chloride raw material with a formula of $MCl_2$ (M=Fe, Co or Ni) is prepared, and dissolved into an anhydrous acetonitrile solvent charged into the glass vessel 11 illustrated in FIG. 1, to form a chloride-acetonitrile solution. Then, calcium carbide minute powders are added and dispersed in the chloride acetonitrile solution in the glass vessel 11 at a molar quantity equal to or a smaller by 1–30 mol % than the molar quantity of the anhydrous chloride, thereby to form a reactive solution.

Herein, the calcium carbide powders are mechanically made into a size of several μm or below. The reactive solution may be formed in another vessel, and then, injected into the glass vessel 11 in FIG. 1, instead of directly forming the reactive solution in the glass vessel 11 as described above.

Then, the reactive solution is heated to a predetermined temperature with the heater 13 with agitating the reactive solution with the rotator 14, to chemically react the anhydrous chloride with the calcium carbide in the reactive solution. In this case, it is required that oxygen and water are not contained into the glass vessel 11 possibly. Therefore, it is desired that an inert gas is introduced into the glass vessel 11 from the gas inlet 16 so that the chemical reaction can be carried out under the inert atmosphere.

Then, in the chemical reaction, the temperature of the reactive solution is monitored with the temperature sensor 13, and the pressure of the glass vessel 11 is monitored with the pressure gauge 17.

A give period of time elapsed, the reactive solution is transferred into a thin polyethylene beaker, and by disposing magnets outside of the wall of the beaker, the black minute powders made of the transition metal acetylide compound are attached onto the wall, and thus, gathered up. The black minute powders are washed sufficiently with anhydrous methanol and anhydrous dichloromethane to remove ion species and remnant calcium carbide. The intended nano-powders made of the transition metal acetylide compound can be provided through the above-mentioned steps.

If the anhydrous chloride is made of $FeCl_2$ to produce nano-powders made of the transition metal acetylide compound with a formula of $FeCl_2$, the heating treatment is preferably carried out within a temperature range of 75–200° C.

If the anhydrous chloride is made of $CoCl_2$ to produce nano-powders made of the transition metal acetylide compound with a formula of $CoCl_2$, the heating treatment is preferably carried out within a temperature range of 75–200° C. In this case, it is desired that the nano-powders are washed with water.

If the anhydrous chloride is made of $NiCl_2$ to produce nano-powders made of the transition metal acetylide compound with a formula of $NiCl_2$, the heating treatment is preferably carried out within a temperature range of 75–160° C.

In any case, if the heating temperature is set to 100° C. or over, the condensation reaction of the solvent may occur, and some by-products may be formed to some degrees. Then, if the heating temperature is set to 150° C. or over, the size of each nano-powder may be increased, e.g., beyond 10 nm. In order to produce minute nano-powders with respective sizes of 10 nm or below, therefore, it is desired that the heating temperature is set to 150° C. or below. In order to prevent the creation of the by-products, it is desired that the heating temperature is set to 100° C. or below.

EXAMPLE

According to the producing steps of the present invention as described above, $FeC_2$ nano-powders, $CoC_2$ nano-powders and $NiC_2$ powders were obtained. Herein, the heating temperature was set within 75–120° C., and the heating period of time was set to 48 hours.

Figure 2:
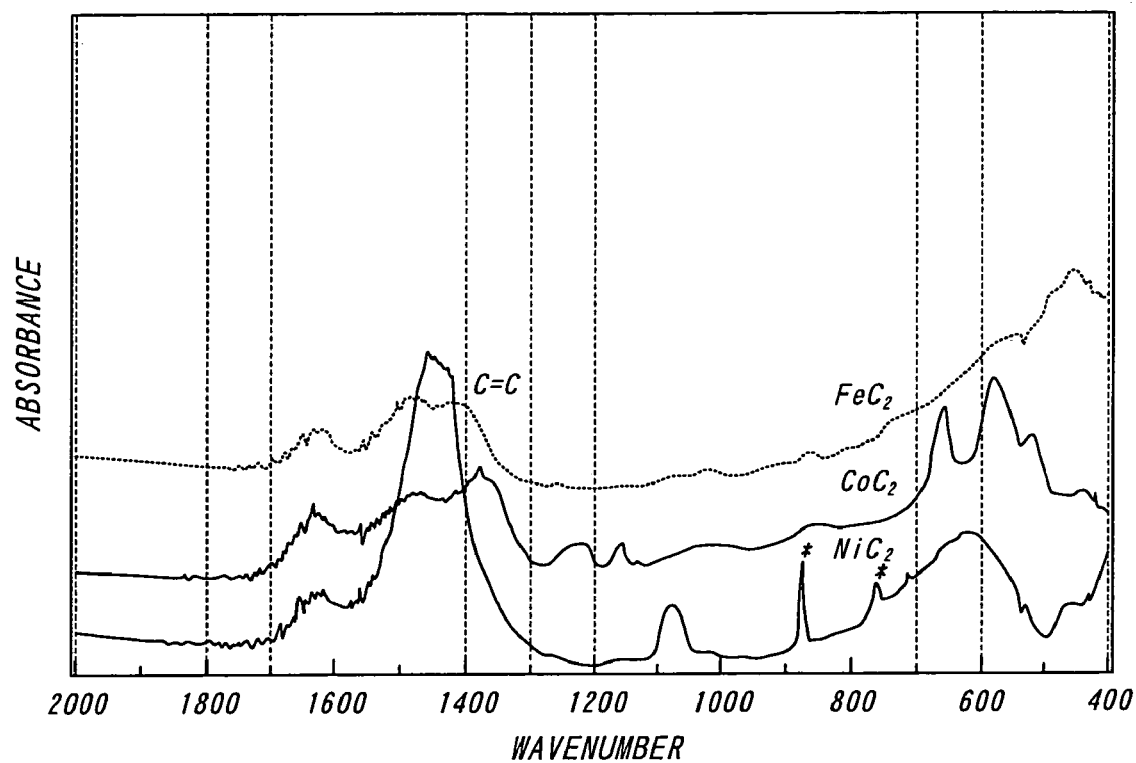
FIG. 2 is a graph illustrating infrared absorption spectra of the nano-powders made of the transition metal acetylide compound according to the present invention.

FIG. 2 is a graph illustrating infrared absorption spectra of the nano-powders. As is apparent from FIG. 2, the infrared absorption spectra exhibit a peak (C≡C peaks) of the respective nano-powders relating to the $C_2^{2-}$ ions. Moreover, since the respective (M-C) stretching vibrations are observed within a frequency range of 700 $cm^{-1}$ or below, it is turned out that all of the nano-powders include M-$C_2$-M bond.

Figure 3:
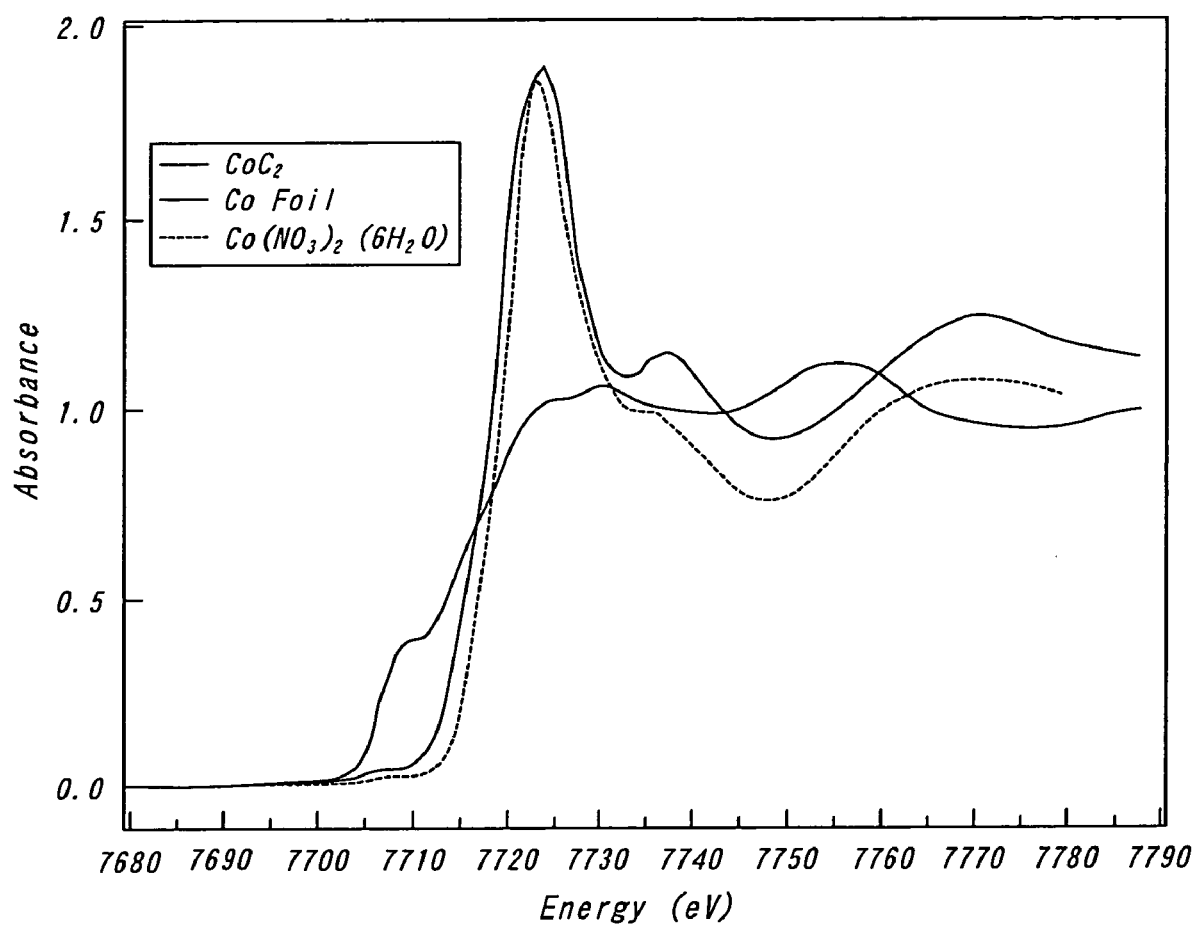
FIG. 3 is a graph illustrating an X-ray absorption spectrum of the $\text{CoC}_2$ nano-powder of the present invention.

FIG. 3 is a graph illustrating an X-ray absorption spectrum of the $CoC_2$ nano-powder. As is apparent from FIG. 3, it is confirmed that the $CoC_2$ nano-powders shows an X-ray absorption spectrum similar to $Co(NO_3)_2 6H_2O$, and the Co element of the $CoC_2$ nano powder exists as a bivalent ion.

Although the present invention was described in detail with reference to the above examples, this invention is not limited to the above disclosure and every kind of variation and modification may be made without departing from the scope of the present invention.

What is claimed is:

1. A transition metal acetylide compound comprising:
   an M-$C_2$-M bond,
   a tetragonal structure, and
   a formula of $MC_2$ (herein, M=Fe or Ni).

2. The transition metal acetylide compound as defined in claim 1, wherein said transition metal acetylide compound exhibit ferromagnetic property.

3. A nano-powder comprising a transition metal acetylide compound having an M-$C_2$-M bond, a tetragonal structure, and a formula of $MC_2$ (herein, M=Fe or Ni).

4. The nano-powder as defined in claim 3, wherein a size of said nano-powder is 5 nm or below.

5. The nano-powder as defined in claim 3, wherein said nano-powder is made of iron acetylide, exhibits super paramagnetic property when a size of a single crystal domain of said nano-powder is 5 nm or below, and exists as a room temperature magnet when said size of said single crystal domain of said nano-powder is within 5–300 nm.

6. The nano-powder as defined in claim 3, wherein said nano-powder is made of nickel acetylide, and exhibits ferromagnetic property below a temperature of 10K.

7. A method for producing a transition metal acetylide compound, comprising the steps of:

dissolving an anhydrous chloride with a formula of $MCl_2$ (M=Fe, Co or Ni) into an anhydrous acetonitrile solvent to form a chionde-acetonitrile solution, adding and dispersing calcium carbide minute powders into said chloride-acetonitrile solution at a molar quantity equal to or smaller by 1–30 mol% than a molar quantity of said anhydrous chloride to form a reactive solution, and heating said reactive solution at a predetermined temperature to chemically react said anhydrous chloride with said calcium carbide minute powders in said reactive solution to form a transition metal acetylide compound having an $M-C_2-M$ bond, a tetragonal structure, and a formula of $MC_2$ (herein, M=Fe, Co or Ni).

8. The producing method as defined in claim 7, wherein said transition metal acetylide compound is formed as a powdery compound.

9. The producing method as defined in claim 8, wherein a size of said transition metallic aertylide compound is set to 10nm or below.

10. The producing method as defined in claim 7, wherein said anhydrous chloride is $FeCl_2$, and said reactive solution is heated within 75–200° C. to chemically react said anhydrous chloride with said calcium carbide minute powers to form an iron acetylide compound having an $Fe—C_2—Fe$ bond, a tetragonal structure, and a formula of $FeC_2$.

11. The producing method as defined in claim 8, wherein said anhydrous chloride is $FeCl_2$, and said reactive solution is heated within 75–200° C. to chemically react said anhydrous chloride with said calcium carbide minute powers to form a powdery iron acetylide compound having an $Fe—C_2—Fe$ bond, a tetragonal structure, and a formula of $FeC_2$.

12. The producing method as defined in claim 11, wherein said powdery iron acetylide compound exhibits super paramagnetic property when a size of a single crystal domain of said powdery iron acetylide compound is set to 5 nm or below, and exists as a room temperature magnet when said size of said single crystal domain of said powdery iron acetylide compound is set within 5–300 nm.

13. The producing method as defined in claim 7, wherein said anhydrous chloride is $CoCl_2$, and said reactive solution is heated within 75–200° C. to chemically react said anhydrous chloride with said calcium carbide minute powers to form a cobalt acetylide compound having a $Co—C_2—Co$ bond, a tetragonal structure, and a formula of $CoC_2$.

14. The producing method as defined in claim 8, wherein said anhydrous chloride is $CoCl_2$, and said reactive solution is heated within 75–200° C. to chemically react said anhydrous chloride with said calcium carbide minute powers to form a powdery cobalt acetylide compound having a $Co—C_2—Co$ bond, a tetragonal structure, and a formula of $CoC_2$.

15. The producing method as defined in claim 11, wherein said powdery cobalt acetylide compound exhibits super paramagnetic property when a size of a single crystal domain of said powdery cobalt acetylide compound is set to 5 nm or below, and exists as a room temperature magnet when said size of said single crystal domain of said powdery cobalt acetylide compound is set within 5–300 nm.

16. The producing method as defined in claim 7, wherein said anhydrous chloride is $NiCl_2$, and said reactive solution is heated within 75–160° C. to chemically react said anhydrous chloride with said calcium carbide minute powers to form a nickel acetylide compound having a $Ni—C_2—Ni$ bond, a tetragonal structure, and a formula of $NiC_2$.

17. The producing method as defined in claim 8, wherein said anhydrous chloride is $NiCl_2$, and said reactive solution is heated within 75–160° C. to chemically react said anhydrous chloride with said calcium carbide minute powers to form a powdery nickel acetylide compound having a $Ni—C_2—Ni$ bond, a tetragonal structure, and a formula of $NiC_2$.

* * * * *